United States Patent
Tada et al.

(10) Patent No.: US 8,741,625 B2
(45) Date of Patent: Jun. 3, 2014

(54) MICROORGANISM AND DEODORIZER CONTAINING THE SAME

(75) Inventors: Nobuki Tada, Miyoshi (JP); Hibiki Matsushita, Nagoya (JP); Toshiaki Kimura, Toyota (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/885,362

(22) PCT Filed: Nov. 9, 2011

(86) PCT No.: PCT/JP2011/006255
§ 371 (c)(1),
(2), (4) Date: May 14, 2013

(87) PCT Pub. No.: WO2012/066749
PCT Pub. Date: May 24, 2012

(65) Prior Publication Data
US 2013/0236415 A1    Sep. 12, 2013

(30) Foreign Application Priority Data

Nov. 15, 2010    (JP) .................................. 2010-255140

(51) Int. Cl.
*C12N 1/20*    (2006.01)
*C12S 3/00*    (2006.01)
*C12S 3/24*    (2006.01)

(52) U.S. Cl.
USPC ........ 435/252.5; 435/262; 435/267; 435/268; 435/836

(58) Field of Classification Search
None
See application file for complete search history.

(56) References Cited

U.S. PATENT DOCUMENTS

| 5,811,287 A * | 9/1998 | Aoshima ..................... 435/252.5 |
| 8,025,874 B2 * | 9/2011 | Bellot et al. .................. 424/93.3 |
| 2009/0275109 A1 | 11/2009 | Bellot et al. |

FOREIGN PATENT DOCUMENTS

| JP | 02-053482 A | 2/1990 |
| JP | 04-262778 A | 9/1992 |
| JP | 07-246381 A | 9/1995 |
| JP | 2810308 B2 | 10/1998 |
| WO | 2008/136545 A1 | 11/2008 |

OTHER PUBLICATIONS

Borowski et al. Przemysl Chemiczny. 2010, 89(4), pp. 318-322; English abstract STN CAPLUS accession No. 2010:774645.*
Takahiro Kanagawa, et al., "Breakdown of dimethyl sulphide by mixed cultures and by *Thiobacillus thioparus*", FEMS Microbiology Letters, 1986, pp. 13-19, vol. 34.
ISao Yumoto, et al., "*Bacillus asahii* sp. nov. a novel bacterium isolated from soil with the ability to deodorize the bad smell generated from short-chain fatty acids", International Journal of Systematic and Evolutionary Microbiology, 2004, pp. 1997-2001, vol. 54.
International Search Report for PCT/JP2011/006255, dated Feb. 27, 2012.

* cited by examiner

*Primary Examiner* — Vera Afremova
(74) *Attorney, Agent, or Firm* — Sughrue Mion, PLLC

(57) ABSTRACT

Thermophilic microorganisms having a deodorizing ability for short chain fatty acids, which are the offensive odor components, are provided. Disclosed are thermophilic microorganisms having a deodorizing ability for short chain fatty acids, which belong to *Bacillus licheniformis*.

6 Claims, 3 Drawing Sheets

| Hit | Id | Description | Score | Bit score | Hit start | Hit end | Hit length | Query enc | Overlap | Identity | %Identity |
|---|---|---|---|---|---|---|---|---|---|---|---|
| FJ641027 | 224021830 | Bacillus licheniformis strain IMAUB1014 16S ribosomal RNA gene, partial sequence | 1,436 | 2,847.15 | 1,452 | 27 | 1,434 | 1,447 | 99.102 | 1,436 | 100 |
| FJ641023 | 224021826 | Bacillus licheniformis strain IMAUB1009 16S ribosomal RNA gene, partial sequence | 1,436 | 2,847.15 | 1,460 | 25 | 1,434 | 1,447 | 99.102 | 1,436 | 100 |
| AY553109 | 47834663 | Bacillus sp. MO16 16S ribosomal RNA gene, partial sequence | 1,436 | 2,847.15 | 1,459 | 28 | 1,440 | 1,447 | 99.516 | 1,440 | 100 |
| AY553107 | 47834661 | Bacillus sp. MO14 16S ribosomal RNA gene, partial sequence | 1,436 | 2,847.15 | 1,459 | 28 | 1,440 | 1,447 | 99.516 | 1,440 | 100 |
| AY553106 | 47834660 | Bacillus sp. GSP83 16S ribosomal RNA gene, partial sequence | 1,436 | 2,847.15 | 1,459 | 28 | 1,440 | 1,447 | 99.516 | 1,440 | 100 |
| AY553104 | 47834658 | Bacillus sp. MO11 16S ribosomal RNA gene, partial sequence | 1,436 | 2,847.15 | 1,472 | 31 | 1,440 | 1,447 | 99.516 | 1,440 | 100 |
| AY505509 | 45934526 | Bacillus licheniformis strain GSP20 16S ribosomal RNA gene, partial sequence | 1,436 | 2,847.15 | 1,466 | 25 | 1,440 | 1,447 | 99.516 | 1,440 | 100 |
| AJ582721 | 39922264 | Bacillus licheniformis partial 16S rRNA gene, isolate R-13577 | 1,436 | 2,847.15 | 1,470 | 29 | 1,440 | 1,447 | 99.516 | 1,440 | 100 |
| HM006908 | 295311580 | Bacillus licheniformis strain Pb-WC09009 16S ribosomal RNA gene, partial sequence | 1,436 | 2,845.17 | 1,491 | 49 | 1,441 | 1,447 | 99.585 | 1,442 | 100 |
| AB425361 | 290350067 | Bacillus sp. S101 gene for 16S rRNA, partial sequence | 1,435 | 2,845.17 | 1,470 | 29 | 1,440 | 1,447 | 99.585 | 1,440 | 100 |
| DQ981804 | 115606194 | Uncultured bacterium clone 1-gw2-su4-210 16S ribosomal RNA gene, partial sequence | 1,435 | 2,845.17 | 1,452 | 6 | 1,445 | 1,447 | 99.862 | 1,445 | 100 |
| DQ981800 | 115606190 | Uncultured bacterium clone 1-gw1-su4-26 16S ribosomal RNA gene, partial sequence | 1,435 | 2,845.17 | 1,470 | 7 | 1,444 | 1,447 | 99.793 | 1,445 | 100 |
| AY553102 | 47834656 | Bacillus sp. MO9 16S ribosomal RNA gene, partial sequence | 1,435 | 2,845.17 | 1,470 | 29 | 1,440 | 1,447 | 99.516 | 1,440 | 100 |
| AY553099 | 47834653 | Bacillus sp. MO6 16S ribosomal RNA gene, partial sequence | 1,435 | 2,845.17 | 1,469 | 28 | 1,440 | 1,447 | 99.516 | 1,440 | 100 |
| GQ222040 | 251510132 | Bacillus licheniformis strain FUA 2028 16S ribosomal RNA gene, partial sequence | 1,434 | 2,843.19 | 1,441 | 4 | 1,436 | 1,447 | 99.24 | 1,437 | 100 |
| GQ205674 | 291220278 | Bacillus licheniformis strain FUA 2027 16S ribosomal RNA gene, partial sequence | 1,434 | 2,843.19 | 1,441 | 4 | 1,439 | 1,443 | 99.24 | 1,437 | 100 |
| HM030744 | 295553695 | Bacillus licheniformis strain B3 16S ribosomal RNA gene, partial sequence | 1,434 | 2,843.19 | 1,489 | 49 | 1,439 | 1,447 | 99.447 | 1,441 | 100 |
| HM006909 | 295311581 | Bacillus licheniformis strain Pb-WC09010 16S ribosomal RNA gene, partial sequence | 1,434 | 2,843.19 | 1,490 | 49 | 1,440 | 1,447 | 99.516 | 1,440 | 100 |
| HM006904 | 295311576 | Bacillus licheniformis strain Pb-WC09004 16S ribosomal RNA gene, partial sequence | 1,434 | 2,843.19 | 1,490 | 49 | 1,440 | 1,447 | 99.516 | 1,440 | 100 |
| HM006903 | 295311575 | Bacillus licheniformis strain Pb-WC09003 16S ribosomal RNA gene, partial sequence | 1,434 | 2,843.19 | 1,490 | 49 | 1,440 | 1,447 | 99.516 | 1,440 | 100 |
| HM006902 | 295311574 | Bacillus licheniformis strain Pb-WC09002 16S ribosomal RNA gene, partial sequence | 1,434 | 2,843.19 | 1,490 | 49 | 1,440 | 1,447 | 99.516 | 1,440 | 100 |
| HM006900 | 295311572 | Bacillus licheniformis strain Pb-SP09003 16S ribosomal RNA gene, partial sequence | 1,434 | 2,843.19 | 1,490 | 49 | 1,440 | 1,447 | 99.516 | 1,440 | 100 |
| HM006898 | 295311570 | Bacillus licheniformis strain Pb-HK09002 16S ribosomal RNA gene, partial sequence | 1,434 | 2,843.19 | 1,490 | 49 | 1,440 | 1,447 | 99.516 | 1,440 | 100 |
| GQ376230 | 262265105 | Bacillus licheniformis strain C3CC 10095 16S ribosomal RNA gene, partial sequence | 1,434 | 2,843.19 | 1,453 | 13 | 1,439 | 1,447 | 99.447 | 1,441 | 100 |
| GQ247891 | 251826436 | Bacillus licheniformis strain x6 16S ribosomal RNA gene, partial sequence | 1,434 | 2,843.19 | 1,471 | 30 | 1,440 | 1,447 | 89.516 | 1,440 | 100 |
| EU231622 | 159144778 | Bacillus licheniformis strain TCCC11009 16S ribosomal RNA gene, partial sequence | 1,434 | 2,843.19 | 1,490 | 49 | 1,440 | 1,447 | 99.516 | 1,440 | 100 |
| EU231767 | 154651141 | Bacillus sp. BS17 16S ribosomal RNA gene, partial sequence | 1,434 | 2,843.19 | 1,445 | 4 | 1,440 | 1,447 | 99.516 | 1,440 | 100 |
| CP000002 | 145902672 | Bacillus licheniformis ATCC 14580, complete genome | 1,434 | 2,843.19 | 1,388 | 9,957 | 1,440 | 1,447 | 99.516 | 1,440 | 100 |
| CP000002 | 145902672 | Bacillus licheniformis ATCC 14580, complete genome | 1,434 | 2,843.19 | 26,056 | 34,655 | 1,440 | 1,447 | 99.516 | 1,440 | 100 |
| CP000002 | 145902672 | Bacillus licheniformis ATCC 14580, complete genome | 1,431 | 2,837.24 | 159,795 | 158,253 | 1,441 | 1,447 | 99.585 | 1,441 | 100 |
| CP000302 | 145902672 | Bacillus licheniformis ATCC 14580, complete genome | 1,431 | 2,837.24 | 922,424 | 920,982 | 1,440 | 1,447 | 99.585 | 1,441 | 100 |
| CP000302 | 145902672 | Bacillus licheniformis ATCC 14580, complete genome | 1,430 | 2,835.26 | 613,488 | 612,047 | 1,441 | 1,447 | 99.516 | 1,441 | 100 |
| CP000002 | 145902672 | Bacillus licheniformis ATCC 14580, complete genome | 1,429 | 2,829.31 | 96,839 | 95,397 | 1,441 | 1,447 | 99.585 | 1,439 | 100 |
| CP000002 | 145902672 | Bacillus licheniformis ATCC 14580, complete genome | 1,427 | 2,829.31 | 3,121,810 | 3,123,252 | 1,443 | 1,447 | 98.724 | 1,440 | 100 |
| EF423509 | 128557693 | Bacillus licheniformis strain BCRC 14353 16S ribosomal RNA gene, partial sequence | 1,434 | 2,843.19 | 1,490 | 51 | 1,438 | 1,445 | 99.378 | 1,438 | 100 |
| AY842869 | 56787103 | Bacillus licheniformis strain C1CC10085 16S ribosomal RNA gene, partial sequence | 1,434 | 2,843.19 | 1,453 | 13 | 1,439 | 1,447 | 99.447 | 1,441 | 100 |
| AE017333 | 52346357 | Bacillus licheniformis DSM 13, complete genome | 1,434 | 2,843.19 | 11,202 | 9,761 | 1,440 | 1,447 | 99.516 | 1,440 | 100 |
| AE017333 | 52346357 | Bacillus licheniformis DSM 13, complete genome | 1,431 | 2,837.24 | 36,900 | 34,459 | 1,441 | 1,447 | 99.585 | 1,440 | 100 |
| AE017333 | 52346357 | Bacillus licheniformis DSM 13, complete genome | 1,431 | 2,837.24 | 159,599 | 158,157 | 1,441 | 1,447 | 99.585 | 1,441 | 100 |
| AE017333 | 52346357 | Bacillus licheniformis DSM 13, complete genome | 1,431 | 2,837.24 | 922,275 | 920,833 | 1,432 | 1,447 | 99.585 | 1,441 | 100 |
| AE017333 | 52346357 | Bacillus licheniformis DSM 13, complete genome | 1,430 | 2,835.26 | 2,835.26 | 613,294 | 1,441 | 1,447 | 99.516 | 1,439 | 100 |
| AE017333 | 52346357 | Bacillus licheniformis DSM 13, complete genome | 1,427 | 2,829.31 | 96,643 | 95,201 | 1,441 | 1,447 | 99.585 | 1,440 | 100 |
| AB020201 | 3925814 | Bacillus sp. DNA for 16S ribosomal RNA, strain TGS1050 | 1,427 | 2,829.31 | 3,121,662 | 3,123,104 | 1,440 | 1,447 | 99.724 | 1,440 | 100 |
| AB425374 | 290350080 | Bacillus sp. SG607 gene for 16S rRNA, partial sequence. Version 2 of two types of sequence | 1,434 | 2,843.19 | 1,490 | 49 | 1,440 | 1,447 | 99.516 | 1,441 | 100 |
| FJ641018 | 224021821 | Bacillus licheniformis strain IMAUB1002 16S ribosomal RNA gene, partial sequence | 1,432 | 2,839.22 | 1,471 | 29 | 1,441 | 1,447 | 99.585 | 1,441 | 100 |
| EU869249 | 195929657 | Bacillus licheniformis strain BG-B11 16S ribosomal RNA (rrs) gene, partial sequence | 1,432 | 2,839.22 | 1,462 | 27 | 1,434 | 1,447 | 99.102 | 1,435 | 100 |
| AB374325 | 290349635 | Bacillus sp. TT402 gene for 16S rRNA, partial sequence, Version 2 of two types of sequence | 1,432 | 2,839.22 | 1,454 | 21 | 1,432 | 1,447 | 90.963 | 1,433 | 100 |
| AB374324 | 290349634 | Bacillus sp. TT104 gene for 16S rRNA, partial sequence, Version 2 of two types of sequence | 1,431 | 2,837.24 | 1,471 | 29 | 1,441 | 1,447 | 99.585 | 1,441 | 100 |
| GU391534 | 284451257 | Bacillus licheniformis strain Na1 16S ribosomal RNA gene, partial sequence | 1,431 | 2,837.24 | 1,437 | 1 | 1,435 | 1,442 | 99.171 | 1,435 | 100 |
| FJ541025 | 224021828 | Bacillus licheniformis strain IMAUB1012 16S ribosomal RNA gene, partial sequence | 1,431 | 2,837.24 | 1,464 | 30 | 1,433 | 1,447 | 99.032 | 1,434 | 100 |
| EU675997 | 188474936 | Bacillus sp. Ephas6 16S ribosomal RNA gene, partial sequence | 1,431 | 2,837.24 | 1,491 | 49 | 1,441 | 1,447 | 99.585 | 1,435 | 100 |
| EF626994 | 118605005 | Bacillus sp. BCL23-1 16S ribosomal RNA gene, partial sequence | 1,431 | 2,837.24 | 1,485 | 43 | 1,441 | 1,447 | 99.585 | 1,441 | 100 |
| DQ981823 | 115606213 | Uncultured bacterium clone 9-gw1-su4-1 16S ribosomal RNA gene, partial sequence | 1,431 | 2,837.24 | 1,445 | 3 | 1,440 | 1,447 | 99.516 | 1,433 | 100 |
| DQ981810 | 115606200 | Uncultured bacterium clone 8-gw1-su4-410 16S ribosomal RNA gene, partial sequence | 1,431 | 2,837.24 | 1,445 | 4 | 1,440 | 1,447 | 99.516 | 1,441 | 100 |
| DQ981796 | 115606186 | Uncultured bacterium clone 1-gw1-su4-4 16S ribosomal RNA gene, partial sequence | 1,431 | 2,837.24 | 1,449 | 4 | 1,444 | 1,447 | 99.793 | 1,444 | 100 |
| DQ480087 | 94467687 | Bacillus licheniformis strain PLLA-2 16S ribosomal RNA gene, partial sequence | 1,431 | 2,837.24 | 1,437 | 1 | 1,435 | 1,442 | 99.171 | 1,435 | 100 |
| AY553103 | 47834657 | Bacillus sp. MO10 16S ribosomal RNA gene, partial sequence | 1,429 | 2,833.28 | 1,470 | 28 | 1,441 | 1,447 | 99.585 | 1,440 | 100 |
| DQ990042 | 116265514 | Bacterium 8-gw2-5 16S ribosomal RNA gene, partial sequence | 1,427 | 2,825.31 | 1,468 | 22 | 1,445 | 1,447 | 99.862 | 1,439 | 99 |

SEQUENCE LISTING

```
<160> NUMBER OF SEQ ID NOS: 1

<210> SEQ ID NO 1
<211> LENGTH: 1447
<212> TYPE: DNA
<213> ORGANISM: Bacillus licheniformis

<400> SEQUENCE: 1
acttccccca atcatctgtc ccaccttcgg cggctggctc caaaaggtta cctcaccgac      60
ttcgggtgtt acaaactctc gtggtgtgac gggcggtgtg tacaaggccc gggaacgtat     120
tcaccgcggc atgctgatcc gcgattacta gcgattccag cttcacgcag tcgagttgca     180
gactgcgatc cgaactgaga acagatttgt gggattggct tagcctcgcg gcttcgctgc     240
cctttgttct gcccattgta gcacgtgtgt agcccaggtc ataaggggca tgatgatttg     300
acgtcatccc caccttcctc cggtttgtca ccggcagtca ccttagagtg cccaactgaa     360
tgctggcaac taagatcaag ggttgcgctc gttgcgggac ttaacccaac atctcacgac     420
acgagctgac gacaaccatg caccacctgt cactctgccc ccgaagggga agccctatct     480
ctagggttgt cagaggatgt caagacctgg taaggttctt cgcgttgctt cgaattaaac     540
cacatgctcc accgcttgtg cgggccccg tcaattcctt tgagtttcag tcttgcgacc     600
gtactcccca ggcggagtgc ttaatgcgtt tgctgcagca ctaaagggcg gaaaccctct     660
aacacttagc actcatcgtt tacggcgtgg actaccaggg tatctaatcc tgttcgctcc     720
ccacgctttc gcgcctcagc gtcagttaca gaccagagag tcgccttcgc cactggtgtt     780
cctccacatc tctacgcatt tcaccgctac acgtggaatt ccactctcct cttctgcact     840
caagttcccc agtttccaat gaccctcccc ggttgagccg ggggctttca catcagactt     900
aagaaaccgc ctgcgcgcgc tttacgccca ataattccgg acaacgcttg ccacctacgt     960
attaccgcgg ctgctggcac gtagttagcc gtggctttct ggttaggtac cgtcaaggta    1020
ccgccctatt cgaacggtac ttgttcttcc ctaacaacag agttttacga tccgaaaacc    1080
ttcatcactc acgcggcgtt gctccgtcag actttcgtcc attgcggaag attccctact    1140
gctgcctccc gtaggagtct gggccgtgtc tcagtcccag tgtggccgat caccctctca    1200
ggtcggctac gcatcgtcgc cttggtgagc cgttacctca ccaactagct aatgcgccgc    1260
gggtccatct gtaagtggta gctaaaagcc accttttatg attgaaccat gcggttcaat    1320
```

```
caagcatccg gtattagccc cggtttcccg gagttatccc agtcttacag gcaggttacc    1380
cacgtgttac tcacccgtcc gccgctgacc taagggagca agctcccgtc ggtccgctcg    1440
acttgca                                                              1447
```

MICROORGANISM AND DEODORIZER CONTAINING THE SAME

CROSS REFERENCE TO RELATED APPLICATIONS

This application is a National Stage of International Application No. PCT/JP2011/006255 filed Nov. 9, 2011, claiming priority based on Japanese Patent Application No. 2010-255140 filed Nov. 15, 2010, the contents of all of which are incorporated herein by reference in their entirety.

TECHNICAL FIELD

The present invention relates to, for example, microorganisms having a deodorizing ability and a deodorizer containing the microorganisms.

BACKGROUND ART

Conventionally, there has been a problem of volatilization of a large amount of offensive odor components when composting organic remnants such as livestock excrement. Examples of the offensive odor component include short chain fatty acids, and even at low concentrations, they are problematic as an offensive odor component.

As a conventional technology relating to the deodorization method, a microbial deodorization technology in which deodorization is conducted using specific microorganisms and complex microorganisms is reported. For example, as to sulfur compounds, decomposition of dimethyl sulfide by a mixed culture product of *Thiobacillus thioparus* and *Pseudomonas* sp. (Takahiro Kanagawa and D. P. Kelly, FEMS Microbiology Letters, 1986, Vol. 34, pp. 13-19) and decomposition of hydrogen sulfide by *Pseudomonas* (JP Patent Publication (Kokai) No. 4-262778A (1992)) are reported. Also, a decomposition method of indole and scatole using *Acinetobacter calcoaceticus* (JP Patent Publication (Kokai) No. 2-53482A (1990)) is reported. While these technologies relating to microbial deodorization of sulfur compounds, indole, and scatole are effective for a partial reduction of the offensive odor components of livestock excrement, etc., they are not sufficient to reduce the offensive odor of, for example, livestock excrement containing a large amount of short chain fatty acids.

Meanwhile, as a microbial deodorization technology for short chain fatty acids, *Bacillus badius* MA001 strain having a deodorizing ability (FERM BP-4493) is known (JP Patent No. 2810308). However, because the optimal activity temperature range for this *Bacillus badius* MA001 strain is close to normal temperature (approximately 15 degrees C. to 45 degrees C.), their effect is dramatically limited when they are used in the process of composting, etc., which is conducted under high-temperature conditions.

SUMMARY OF INVENTION

Technical Problem

In order to achieve microbial deodorization of short chain fatty acids, which are the offensive odor components during the process of composting, microorganisms that actively function under high-temperature conditions in the process of composting are necessary.

In view of the aforementioned circumstance, an object of the present invention is to provide thermophilic microorganisms having a deodorizing ability for short chain fatty acids, which are the offensive odor components.

Solution to Problem

We conducted intensive research in order to solve the aforementioned problem. As a result, we have found thermophilic microorganisms having a deodorizing ability for short chain fatty acids, thereby completing the present invention.

That is, the present invention provides thermophilic microorganisms having a deodorizing ability for short chain fatty acids, which belong to *Bacillus licheniformis*, such as those specified by the accession number NITE BP-998. Here, examples of the short chain fatty acid to be deodorized include one or more kinds selected from the group consisting of propionic acid, butyric acid (n-butanoic acid), valeric acid (n-pentanoic acid), and isovaleric acid (3-methylbutanoic acid).

Also, the present invention provides a deodorizer comprising the aforementioned microorganisms as an active ingredient. The microorganisms contained in the deodorizer can be carried by microorganism carriers.

Further, the present invention provides a production method of compost comprising the step of adding the aforementioned microorganisms or deodorizer to organic remnants.

The contents as disclosed in the description and/or drawings of Japanese Patent Application No. 2010-255140, to which the present application claims priority, are incorporated herein.

Advantageous Effects of Invention

According to the present invention, the production of short chain fatty acids, which are the offensive odor components, can be reduced, and thereby deodorization is achieved in the process of composting, etc.

BRIEF DESCRIPTION OF DRAWINGS

FIG. 1-1 is a diagram showing the results of homology analysis of the 16S rRNA gene of TAB7 strain.

FIG. 1-2 is the continuation of FIG. 1-1.

FIG. 2 shows graphs indicating the decomposition of short chain fatty acids in livestock excrement by the microbial materials carrying TAB7 strain.

DESCRIPTION OF EMBODIMENTS

Figure 2:
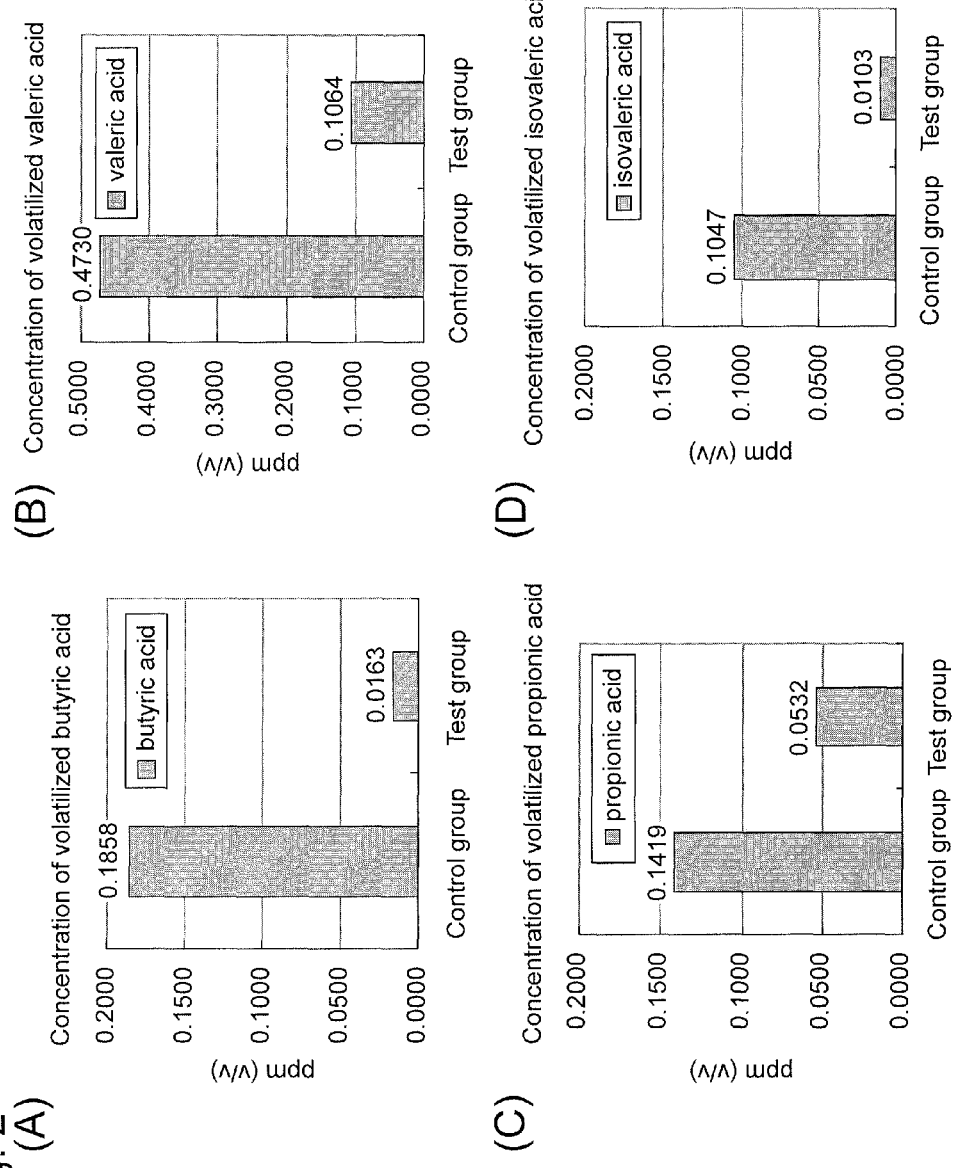

Hereinbelow, the present invention will be described in detail.

The microorganisms of the present invention are thermophilic microorganisms having a deodorizing ability for short chain fatty acids, which belong to *Bacillus licheniformis*. Here, the "deodorizing ability for short chain fatty acids" refers to an ability to deodorize the offensive odor of short chain fatty acids by decomposing and reducing the short chain fatty acids. Also, the "thermophilic microorganisms" refer to microorganisms capable of growing under a high-temperature condition of 50 degrees C. or higher (for example, 50 degrees C. to 60 degrees C., preferably 55 degrees C. to 60 degrees C.). The microorganisms of the present invention are thermophilic and actively function under a high-temperature condition of 50 degrees C. or higher in the process of composting, and can decompose short chain fatty acids, which become problematic as an offensive odor components during composting (i.e., the production of compost), whereby deodorizing the offensive odor produced during the process of composting or emitted by the resulting compost.

Although no particular limitation is imposed on the short chain fatty acid to be decomposed by the microorganisms of the present invention, examples thereof include acetic acid, propionic acid, butyric acid (n-butanoic acid), isobutyric acid (2-methylpropionic acid), valeric acid (n-pentanoic acid), hydrangelic acid (2-methylbutanoic acid), isovaleric acid (3-methylbutanoic acid), pivalic acid (2,2-dimethylpropionic acid), caproic acid (n-hexanoic acid), enanthic acid (n-heptanoic acid), caprylic acid (n-octanoic acid), pelargonic acid (n-nonanoic acid), and capric acid (n-decanoic acid). Particular examples include one or more kinds selected from propionic acid, butyric acid (n-butanoic acid), valeric acid (n-pentanoic acid), and isovaleric acid (3-methylbutanoic acid).

As the source from which the microorganisms of the present invention are isolated, for example, livestock excrement in the process of composting is used. From livestock excrement in the process of composting, microorganisms belonging to *Bacillus licheniformis* that actively function in the livestock excrement and can grow under a high-temperature condition, and is capable of efficiently decomposing short chain fatty acid and thereby deodorizing it can be isolated as the microorganisms of the present invention. Examples of the evaluation method for the deodorizing ability of the isolated microorganisms include a method including adding the isolated microorganisms to a short chain fatty acid-containing medium and culturing them, and after culturing, measuring the amount of short chain fatty acid in the culture product by gas chromatograph-mass spectrometry, etc. When the amount of short chain fatty acid in the culture product to which the microorganisms have been added is significantly reduced, then the microorganisms can be determined to have a deodorizing ability for short chain fatty acid. TAB7 strain belonging to *Bacillus licheniformis* could be successfully isolated by this method.

TAB7 strain was deposited at Incorporated Administrative Agency National Institute of Technology and Evaluation, Patent Microorganisms Depositary (NPMD) (2-5-8 Kazusakamatari, Kisarazu-shi, Chiba 292-0818, Japan) on Oct. 29, 2010, under the accession number NITE P-998, and was then converted to a deposit under the Budapest Treaty at Incorporated Administrative Agency National Institute of Technology and Evaluation, Patent Microorganisms Depositary (NPMD), on Sep. 28, 2011, under the accession number NITE BP-998. The TAB7 strain was identified as a novel bacterial strain belonging to *Bacillus licheniformis* according to the bacteriological properties and the homology analysis of the 16S rRNA gene, etc., which will be presented in Examples later. It is to be noted that a thermophilic mutant of TAB7 strain obtained by spontaneous or artificially-induced mutation that retains a deodorizing ability for short chain fatty acid is encompassed by the microorganisms of the present invention.

For example, the TAB7 strain can be cultured and grown in a medium containing 1% glucose, 1% yeast extract, 0.1% $Na_2HPO_4$, and 0.1% $(NH_4)_2SO_4$ under conditions of a pH of 6.0 to 9.0 (for example, a pH of 7.0) and a temperature of 25 degrees C. to 55 degrees C. (preferably, 45 degrees C. to 52 degrees C.). It is to be noted that the medium used for culturing TAB7 strain may be any of a number of nutrient media employed in general fermentation technology. For example, a medium containing an organic nutrient source such as broth and peptone and a trace amount of inorganic nutrient source can be used for culturing TAB7 strain.

Meanwhile, the deodorizer of the present invention is a deodorizer containing the aforementioned microorganisms of the present invention as an active ingredient. For example, the offensive odor generated during the process of composting or the offensive odor of compost can be deodorized by adding the deodorizer of the present invention to the livestock excrement in the process of composting and the compost. As the microorganisms of the present invention in the deodorizer, those carried by microorganism carriers can also be used. Although no particular limitation is imposed on the microorganism carrier, examples thereof include perlite, bentonite, zeolite, vermiculite, diatomaceous earth, peat moss, and activated carbon. For example, 100 ml of a culture liquid of the microorganisms of the present invention (the absorbance value at OD 660 nm is approximately 2.0) is added to 1 kg of perlite, followed by stirring for approximately five minutes, whereby the microorganisms of the present invention are allowed to adsorb to the perlite. Further, in addition to the microorganisms of the present invention, the deodorizer of the present invention can contain additives such as starch, oil, bran, sawdust, cellulose, carbohydrate, chitin, gelatin, calcium carbonate, calcium sulfate, magnesium carbonate, activated carbon, diatomaceous earth, zeolite, glass, nylon, urethane, and polyester.

Further, the production method of compost of the present invention (hereinbelow, referred to as "the present method") is a production method of compost that utilizes the aforementioned microorganisms or deodorizer of the present invention, wherein organic remnants to which the microorganisms or deodorizer has been added are subjected to composting. According to the present method, the offensive odor emitted by short chain fatty acid during composting can be deodorized, and thus compost with little or absolutely no offensive odor can be provided. Examples of the organic remnant used for composting include excrement or a mixture of feces and urine of animals including excrement of humans and livestock (such as pigs, cows, and chickens).

In the present method, for example, to the organic remnants in which the water content is appropriately adjusted in advance (for example, to a water content ratio of approximately 60%), the microorganisms of the present invention or the deodorizer of the present invention containing the microorganisms are added in an amount of $10^5$ to $10^{13}$ bacteria per kg of organic remnant. The addition can be done at any time before composting. Subsequently, the organic remnants to which the microorganisms or deodorizer of the present invention has been added are subjected to composting. Composting is carried out by, for example, subjecting a mixture of the microorganisms or deodorizer of the present invention and the organic remnants to fermentation. Examples of the fermentation condition include a temperature of 40 degrees C. to 75 degrees C. (preferably 50 degrees C. to 60 degrees C.) and a period of two to five weeks (preferably three to five weeks). By this process, the offensive odor emitted by short chain fatty acid during the process of composting can be reduced, and compost with little or absolutely no offensive odor of short chain fatty acid can be produced.

Examples of the evaluation method for the offensive odor of short chain fatty acid in the compost during composting by the present method or the offensive odor of short chain fatty acid in the compost produced by the present method include a method of measuring the amount of short chain fatty acid in the compost during composting or the compost thus produced by gas chromatograph-mass spectrometry, etc. When the amount of short chain fatty acid is significantly reduced compared to the compost during composting using organic remnants to which neither the microorganisms nor the deodorizer of the present invention is added or the compost thus produced, then the compost during composting by the present method or the compost produced by the present method can be determined to have reduced unpleasant odor, and thus be favorable.

Alternatively, the offensive odor of short chain fatty acid in the compost can be organoleptically evaluated. That is, a plurality of people check the odor of the compost during composting by the present method or the odor of the compost produced by the present method, and when it is determined that the offensive odor is significantly reduced or completely absent compared to the compost during composting using organic remnants to which neither the microorganisms nor the deodorizer of the present invention is added or the compost thus produced, then the compost during composting by the present method or the compost produced by the present method can be determined to have reduced unpleasant odor, and thus be favorable.

EXAMPLE

Hereinafter, the present invention will be described in more detail with reference to Examples; however, the technical scope of the present invention is not limited to these Examples.

Example 1

Isolation of Microorganisms Efficiently Decomposing and Deodorizing Short Chain Fatty Acids and Taxonomic Properties of the Microorganisms 1-1. Isolation of Microorganisms In order to search for microorganisms that vigorously act in the composting and are capable of efficiently decomposing and deodorizing the offensive odor components in the process of composting, livestock excrement in the process of composting was obtained from livestock farmers throughout Japan and isolation of offensive odor-reducing microorganisms was attempted.

As a result, microorganisms capable of actively functioning in the livestock excrement and growing under high-temperature conditions that can efficiently decompose and deodorize short chain fatty acids were acquired. The bacterial strain thus obtained is referred to as TAB7 strain.

1-2. Physiological Properties of TAB7 Strain

The bacteriological properties of TAB7 strain were investigated using the methods described in "BERGEY'S MANUAL of Systematic Bacteriology, volume three" and "Manual for the Identification of Medical Bacteria, third edition" and by a test using API50CHB (bioMerieux, Lyon, France). As a result, the following findings were obtained.

TABLE 1

Growth and morphological findings and bacteriological properties of TAB7 strain

<Morphological properties>

| Cell morphology | *Bacillus* (0.8-0.9 × 1.2-2.0 μm) |
| Gram staining | + |
| Spore formation | + |
| Motility | + |

TABLE 1-continued

Growth and morphological findings and bacteriological properties of TAB7 strain

<Culture properties>

| Colony morphology | Medium: nutrient agar<br>Culture time: 24 h<br>Diameter: 2.0-3.0 mm<br>Color: Light yellow<br>Shape: Oval<br>Elevation: Lenticular<br>Margin: Undulate<br>Surface shape, etc.: Smooth<br>Transparency: Opaque<br>Viscosity: Butter-like |
| Culture temperature range | 25° C.: +<br>30° C.: +<br>37° C.: +<br>45° C.: +<br>50° C.: +<br>55° C.: +<br>60° C.: − |
| Culture pH range | pH 5: −<br>pH 6: +<br>pH 7: +<br>pH 8: +<br>pH 9: + |

<Physiological properties>

| Catalase | + |
| Oxidase | − |
| Acid/gas production (glucose) | −/− |
| O/F test (glucose) | −/− |
| Growth in 10%NaCl | + |
| Casein hydrolysis | + |
| Starch hydrolysis | + |
| Beta-galactosidase | + |
| Arginine dihydrolase | + |
| Lysine decarboxylase | − |
| Ornithine decarboxylase | − |
| Citric acid utilization | − |
| $H_2S$ production | − |
| Urease | − |
| Tryptophan deaminase | − |
| Indole production | − |
| Acetoin production | − |
| Gelatinase | − |
| NIT Nitrate reduction | − |

<Fermentation test>

| Glycerol | + |
| Erythritol | − |
| D-Arabinose | − |
| L-Arabinose | + |
| Ribose | + |
| D-Xylose | − |
| L-Xylose | − |
| Adonitol | − |
| Beta-methyl-D-xylose | − |
| Galactose | − |
| Glucose | + |
| Fructose | + |
| Mannose | + |
| Sorbose | − |
| Rhamnose | − |
| Dulcitol | − |
| Inositol | − |
| Mannitol | + |
| Sorbitol | + |
| Alpha-methyl-D-mannoside | − |
| Alpha-methyl-D-glucoside | + |
| N-Acetylglucosamine | + |
| Amygdalin | + |
| Arbutin | + |
| Esculin | + |
| Salicin | + |
| Cellobiose | + |
| Maltose | + |
| Lactose | − |
| Melibiose | − |

TABLE 1-continued

Growth and morphological findings and bacteriological properties of TAB7 strain

| | |
|---|---|
| Saccharose | + |
| Trehalose | + |
| Inulin | − |
| Melicitose | − |
| Raffinose | − |
| Starch | − |
| Glycogen | − |
| Xylitol | − |
| Gentiobiose | + |
| D-Turanose | − |
| D-Lyxose | − |
| D-Tagatose | + |
| D-Fucose | − |
| L-Fucose | − |
| D-Arabitol | − |
| L-Arabitol | − |
| Gluconate | − |
| 2-Ketogluconate | − |
| 5-Ketogluconate | − |

+: Positive −: Negative

As is understood from the bacteriological properties shown in Table 1, TAB7 strain is motile gram positive bacteria, and it forms spores but did not show swelling of the bacterial body due to the spores. It was positive for catalase reaction and negative for oxidase reaction. These properties were consistent with the general properties of the genus *Bacillus*.

Further, TAB7 strain fermented glycerol, ribose, fructose, and the like, while it did not ferment L-xylose, galactose, and the like. Also, it exhibited the beta-galactosidase and arginine dihydrolase activities; did not produce acetoin; did not exhibit the gelatinase activity; and did not reduce nitrate. Further, TAB7 strain grew in 10% NaCl and hydrolyzed casein and starch. These properties were confirmed to be largely consistent with the properties of *Bacillus licheniformis*, which was suggested by an identification test based on the 16S rRNA gene to be described later. However, there were differences, and particularly, the difference is that TAB7 strain neither produced acetoin nor hydrolyzed gelatin. In this aspect, TAB7 strain was observed to be different from known *Bacillus licheniformis* strains.

1-3. Taxonomic Identification of TAB7 Strain by 16S rRNA Gene Sequence

In order to perform classification and identification of TAB7 strain based on the gene sequence, the 16S rRNA gene was obtained from the genomic DNA of TAB7 strain and the nucleotide sequence of the gene was determined in accordance with the method described in Biseibutsugaku jikkenho (literal translation: microbiological experimental technique) (Kodansha Ltd.). A part of the nucleotide sequence of the 16S rRNA gene of TAB7 strain thus identified is shown as the nucleotide sequence of SEQ ID NO: 1.

Also, a BLAST search was performed for the nucleotide sequence of the 16S rRNA gene of the TAB7 strain against the DNA nucleotide sequence data base (NCBI (GenBank)). The results are shown in FIGS. 1-1 and 1-2. As shown in FIGS. 1-1 and 1-2, TAB7 strain showed the highest homology to *Bacillus licheniformis*.

From the above results, TAB7 strain was identified as a novel bacterial strain of *Bacillus licheniformis*.

1-4. Confirmation of the Growth of TAB7 Strain in Livestock Excrement

In order for TAB7 strain to steadily function in the process of composting, it is necessary that TAB7 strain grows in the livestock excrement components. In view of this, the growth of TAB7 strain was examined using actual livestock excrement.

From each of the pig excrement (a water content ratio of approximately 60%) and the chicken excrement (a water content ratio of approximately 60%) collected from a working farm, 100 g was weighed. Then, after adding 400 mL of purified water to the livestock excrement, an agar for a medium was added so that the content thereof was 1.5%, and the resulting mixture was subjected to autoclave sterilization (at 121 degrees C. for 20 minutes).

After the autoclave sterilization, the mixture was cooled to approximately room temperature, and in a clean room, it was added to a sterilized petri dish and solidified.

Into the livestock excrement medium prepared as above, TAB7 strain was seeded using a platinum loop and cultured at 50 degrees C. for 12 hours, and it was confirmed that TAB7 strain grew in the livestock excrement components without a problem.

Example 2

Decomposition of Short Chain Fatty Acids in Livestock Excrement by TAB7 Strain

2-1. Culture of TAB7 Strain

The necessary amount of TAB7 strain was cultured and proliferated in a culture medium containing the components as shown in Table 2 below.

TABLE 2

| Culture medium components: | |
|---|---|
| (1) glucose | 1% |
| (2) yeast extract | 1% |
| (3) $Na_2HPO_4$ | 0.1% |
| (4) $(NH4)_2SO_4$ | 0.1% |

The above culture medium components were dissolved in purified water and the pH was adjusted to 7.0, and the resulting solution was kept at 121 degrees C. for 15 minutes using an autoclave for sterilization.

Subsequently, 300 mL of the medium thus produced was added to a 500 ml baffled flask, into which a small amount of TAB7 strain was seeded from the glycerol stock that was produced in advance. After culturing at 50 degrees C. for 16 hours while stirring, a culture liquid of TAB7 strain with an absorbance value of approximately 2.0 (OD 660 nm) was obtained.

2-2. Attachment of TAB7 Strain to Microorganism Carriers

To 1 kg of perlite (the microorganism carrier), 100 ml of the culture liquid of TAB7 strain obtained in the above 2-1 section was added. The resulting mixture was then stirred for five minutes to allow TAB7 strain to adsorb onto perlite, whereby the microbial materials were obtained.

2-3. Decomposition of Short Chain Fatty Acids in Livestock Excrement by the TAB7 Strain-Carrying Microbial Materials Fresh excrement (a water content ratio of approximately 70%) of three- to six-month-old pigs was obtained from a pig farm, and using dried excrement (a water content ratio of approximately 20%) for adjustment of water content, the excrement was adjusted to have a water content ratio of approximately 60%.

To nine kg of the water content-adjusted pig excrement, 18 g of the microbial materials produced in the above 2-2 section were added (approximately $10^7$ live TAB7 strain bacteria were present per g of the microbial material) to serve as a test group (contained approximately $2 \times 10^4$ TAB7 strain per g of livestock excrement). Also, a group containing pig excrement with nothing added thereto was used as a control group.

These excrements were composted using the small size composting experiment unit, KAGUYAHIME (the product of Fujihira Industry Co., Ltd.). The concentration of short chain fatty acid, which is the offensive odor component, in the pig excrement was measured after approximately four days for composting.

For the measurement of the concentration of short chain fatty acid, firstly, the water content ratio in the collected compost sample was measured, and after keeping it in the headspace at 60 degrees C. for 30 minutes (vial 22 ml), the gas thus volatilized was analyzed by gas chromatograph-mass spectrometer K9 (the product of JEOL Ltd.) to quantify the amount of short chain fatty acid in the compost (the column used: TC-WAX, ID 0.32 mm, 30 m, the product of GL Sciences Inc.). The amount of short chain fatty acid thus quantified is shown in FIG. 2.

In FIG. 2, each panel represents the following; (A): the concentration of volatilized butyric acid in the compost, (B): the concentration of volatilized valeric acid in the compost, (C): the concentration of volatilized propionic acid in the compost, and (D): the concentration of volatilized isovaleric acid in the compost.

As shown in FIG. 2, compared to the control group (the no-microbial material-added group), butyric acid, valeric acid, propionic acid, and isovaleric acid were confirmed to have decreased by 90.1%, 77.5%, 62.5%, and 90.1%, respectively, in the compost of the test group (the microbial material-added group).

REFERENCE TO DEPOSITED BIOLOGICAL MATERIAL

NITE BP-998

All publications, patents, and patent applications cited herein are incorporated herein by reference in their entirety.

The invention claimed is:

1. An isolated thermophilic microorganism having a deodorizing ability for short chain fatty acid, which belongs to *Bacillus licheniformis*, wherein said microorganism is the microorganism which is specified by the accession number NITE BP-998.

2. The microorganism according to claim 1, wherein the short chain fatty acid is one or more kinds selected from the group consisting of propionic acid, butyric acid, valeric acid, and isovaleric acid.

3. A deodorizer comprising the microorganism according to claim 1 as an active ingredient.

4. The deodorizer according to claim 3, wherein the microorganism is carried by a microorganism carrier selected from the group consisting of perlite, bentonite, zeolite, vermiculite, diatomaceous earth, peat moss and activated carbon.

5. A production method of compost comprising the step of adding the microorganism according to claim 1 to excrement or a mixture of feces and urine of animals.

6. A production method of compost comprising the step of adding the deodorizer according to claim 3 to excrement or a mixture of feces and urine of animals.

* * * * *